United States Patent [19]

Cary, Jr. et al.

[11] 4,219,367

[45] Aug. 26, 1980

[54] SURGICAL PREP HAND CLEANING

[76] Inventors: George R. Cary, Jr.; Stocker R. Cary, both of 3439 Prytania St., Room 205, New Orleans, La. 70115

[21] Appl. No.: 949,388

[22] Filed: Oct. 5, 1978

[51] Int. Cl.² ............................................. B08B 3/02
[52] U.S. Cl. ......................................... 134/29; 4/628;
4/653; 134/36; 134/199; 239/10; 239/101;
239/310; 239/543; 4/615
[58] Field of Search .................... 134/29, 93, 36, 40,
134/199; 422/28, 266; 4/1, 166, 187 R; 239/10,
101, 102, 310, 543, 544, 545

[56] References Cited

U.S. PATENT DOCUMENTS

| 605,929 | 6/1898 | Smead | 134/93 |
|---|---|---|---|
| 870,766 | 11/1907 | Eaton | 134/199 UX |
| 2,616,095 | 11/1952 | Stuckey | 4/166 |
| 2,665,171 | 1/1954 | Stievater | 239/543 X |
| 2,775,774 | 1/1957 | Lugan | 4/166 |
| 3,576,277 | 4/1971 | Blackmon | 4/1 X |
| 3,614,244 | 10/1971 | Eck | 239/310 X |
| 3,699,984 | 10/1972 | Davis | 134/199 X |
| 3,728,745 | 4/1973 | Brendgord et al. | 4/166 |
| 3,757,806 | 9/1973 | Bahskar et al. | 134/36 X |
| 3,992,730 | 11/1976 | Davis | 4/187 R |

OTHER PUBLICATIONS

Bhaskar et al, "Pulsating Water Jet Devices . . . ;" *Military Medicine,* Mar. 1971, vol. 136, No. 3, pp. 264–266.
Bhaskar et al, "Effect of High Pressure Water Jet . . . " *The Journal of Periodontology—Periodontics,* 1969, vol. 40, pp. 35/593–40/598.
Bhaskar et al. "Water Jet Devices in Dental Practice", *The Journal of Periodontology—Periodontics,* Oct. 1971, pp. 658–664.
Decker et al, "A Rapid Method for the Presurgical Cleaning of Hands" *Obstetrics—Gynecology;* Jan. 1978; vol. 51, No. 1, pp. 115–117.
Gross et al, "Evaluation of Two Antiseptic Agents . . . ;" *The American Journal of Surgery;* Jul. 1973; vol. 126, pp. 49–52.
Cutright et al, "A New Method of Presurgical Hand Cleansing" *Oral Surgery, Oral Medicine, Oral Pathology,* Feb. 1972; vol. 33, No. 2, pp. 162–167.
Gross et al, "The Effect of Pulsating Water Jet Lavage . . ." *Journal of Oral Surgery;* Mar. 1971; vol. 29, pp. 187–190.

*Primary Examiner*—Richard V. Fisher
*Attorney, Agent, or Firm*—Cushman, Darby & Cushman

[57] ABSTRACT

Apparatus and method for facilitating the washing of a person's hands to achieve surgical cleanliness in a simple, effective manner. A transparent hollow sphere has a pair of hand openings formed in it, with a pair of pulsating water jet spray heads mounted on the sphere to direct intersecting sprays of water onto a person's hands placed through the hand openings in the sphere. One spray head is mounted in substantially the same horizontal plane as the hand openings, and between them, and the other spray head is mounted in substantially the same vertical plane as the one spray head, about 60° to 135° around the circumference of the sphere with respect to the one spray head. By operating a foot pedal, water is delivered under pressure to the spray heads which pulse the water onto the person's hands, the water then draining through an opening in the bottom of the sphere to be sewered. A soap dispenser may be provided within the sphere.

13 Claims, 2 Drawing Figures

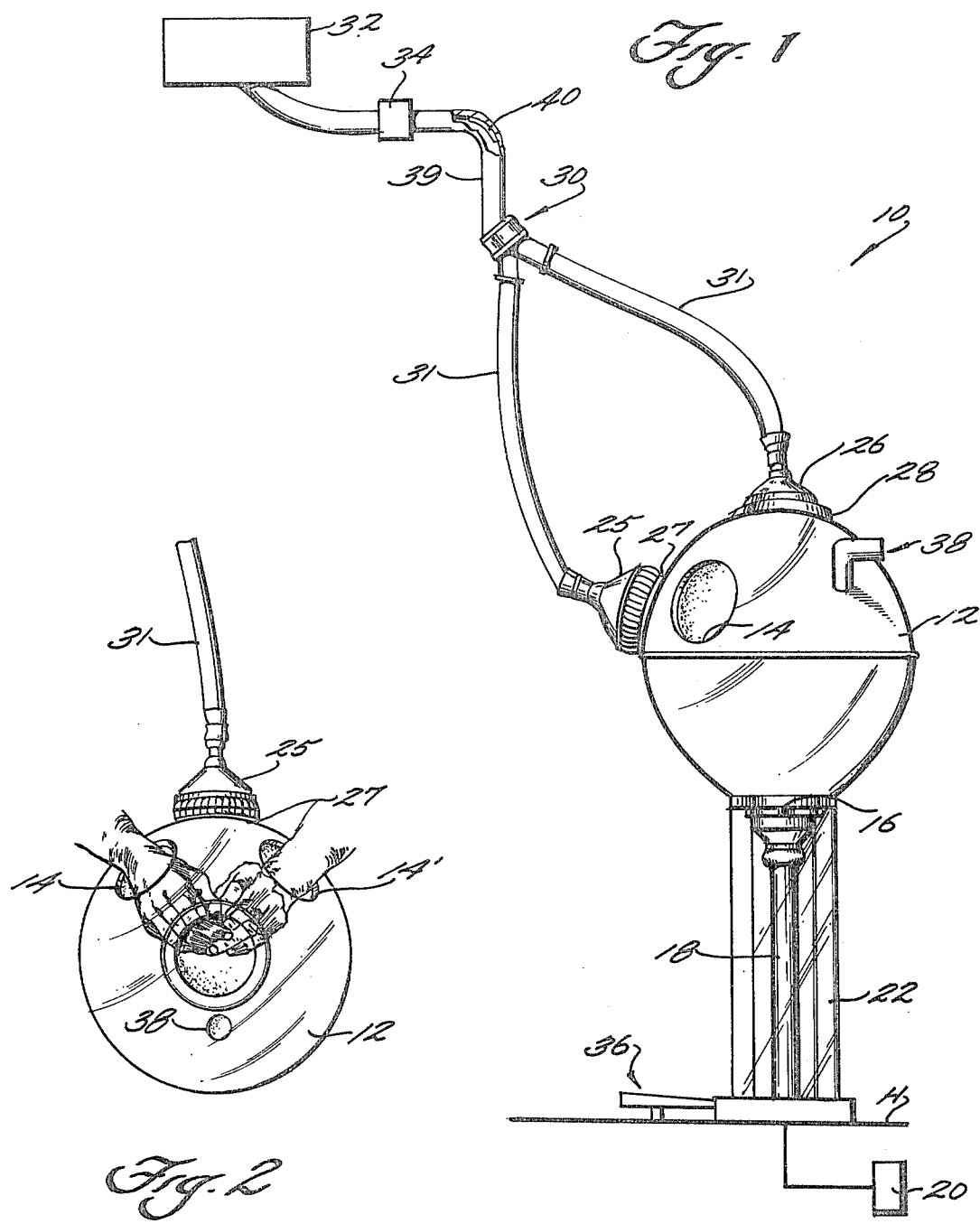

SURGICAL PREP HAND CLEANING

BACKGROUND AND SUMMARY OF THE INVENTION

The traditional method for presurgical cleansing of hands is a standard brush scrub of about five to fifteen minutes duration using surgical soap, and applying mechanical force to the hands. Typical systems facilitating such conventional procedures are shown in U.S. Pat. Nos. 2,616,095; 3,576,277; 3,728,745; and 3,992,730. Variations of the same method are of course used by food handlers in commercial food processing and serving facilities, and by individuals in public rest rooms, soap being applied to the hands while the hands are scrubbed and placed under a direct water stream. It has been found, however, that by applying high pressure pulsating jets of a Betadine solution, or the like, onto a person's hands, surgical cleanliness comparable to that achieved in a conventional ten minute brush scrub can be achieved in about ninety seconds, with less irritation to the skin, and greater consistency of bacteria elimination. Such a procedure is reported in *Obstetrics-Gynecology* Vol. 51, No. 1, January 1978 (Harper and Row Publishers), pages 115 through 117, "A Rapid Method for the Presurgical Cleansing of Hands" by Decker, et al. Despite the advantageous results achievable by employing such a method; however, it has not met with widespread acceptance, but has been confined to clinical settings.

According to the present invention, an apparatus, and method of utilization of same, are provided for facilitating the washing of a person's hands by directing sprays of pulsating water which compress and decompress the skin surfaces, debris being bounced off the skin by trampoline effect, that is simple and easy to install for use in a wide variety of facilities including hospital scrub areas, commercial food handling facilities, and even public rest rooms.

According to the present invention, an apparatus is provided for facilitating the washing of a person's hands simply and quickly, with no effort, in as short a time as fifteen to twenty seconds. The apparatus includes a chamber and means defining a pair of horizontally spaced and substantially vertically coincident openings in the chamber for receiving a person's hands therein. A pair of pulsating water jet spray heads capable of delivering water at generally about 70 psi (preferably 50 to 100 psi) at a pulsing rate of generally about 800 pulses per minute (preferably 800 to 1200 pulses per minute) are mounted in the chamber so that the heads direct jets of water therefrom into the volume defined by the chamber, and so that the jets of water intersect in the volume. The heads are disposed in a common vertical plane between the chamber hand openings, and a drain opening is provided in a lower portion of the chamber. Preferably, the spray heads are mounted so that the jets issuing therefrom make an angle of about 60° to about 135° with respect to each other, one of the jets preferably being disposed in substantially the same horizontal plane as the hand openings, and therebetween, while the other spray head is mounted so that the jets issuing therefrom have a downward velocity component.

The chamber provided according to the present invention most suitably is formed as a sphere, mounted a predetermined height off the ground by a support. Water is supplied to the spray heads through a valve which is controlled by a foot pedal operated by a person using the apparatus. While this spraying action can result in the desired degree of hand cleanliness without the use of any soap solution—merely pure water—if desired a conventional soap dispensing arrangement may be provided that is accessible within the spherical chamber so that the person washing his hands may apply soap thereto before the spraying action is initiated, or during spraying. Alternatively, the water flow can be past a solid form of sterilizing composition, the water picking up some of the composition when flowing therepast to the spray heads. The sprayed liquid is withdrawn from the chamber through a drain opening, and sewered, there being no necessity for recycling of the liquid since only pure water is used.

Thus, according to the present invention, it is possible to simply and easily effect cleaning of a person's hands even to surgical cleanliness in a matter of seconds, and utilizing apparatus that is simple and inexpensive, having wide applicability.

It is the primary object of the present invention to provide simple apparatus and a simple method for facilitating washing of a person's hands. This and other objects of the invention will become clear from an inspection of the detailed description of the invention, and from the appended claims.

BRIEF DESCRIPTION OF THE DRAWINGS

FIG. 1 is a side view, partly diagrammatic, illustrating exemplary apparatus according to the present invention; and FIG. 2 is a top view of the apparatus of FIG. 1, with the top spray head removed for clarity, showing the user's hands in place in the apparatus.

DETAILED DESCRIPTION OF THE DRAWINGS

Exemplary apparatus for facilitating the washing of a person's hands according to the present invention is shown generally at 10 in the drawings. The apparatus 10 is simple and efficient, and essentially takes up no more space than a conventional wash basin, yet employs recently developed procedures for effecting rapid, nonirritating, cleansing of a person's hands—even to surgical cleanliness standards. Since the apparatus 10 is simple and does not take up much space, it is not confined to the presurgical cleansing environment, but is applicable to a wide variety of environments such as commercial food handling facilities, public rest rooms, and virtually every other place where conventional wash basins are now utilized.

The apparatus 10 according to the present invention includes a chamber 12 with means defining a pair of hand openings, 14, 14', that allow a person to insert their hands within the chamber 12 (see FIG. 2). The chamber 12 preferably comprises a transparent, rigid, hollow sphere, and the hand openings 14, 14', may be defined by cuffs of flexible material (not shown) which retard the splashing of liquid out of the chamber 12 through the hand openings 14, 14'. Means defining a drain opening 16 are provided in the bottom of the sphere 12. Preferably, a drain pipe 18 leads downwardly from the drain opening 16, and support means 22 are provided (substantially concentric with the drainpipe 18) for supporting the chamber 12 at a vertically raised position from the floor H, or other horizontal surface, so that the chamber 12 is at the proper height for ready utilization.

Pulsating jets of water are directed into the interior of the chamber 12, on a person's hands therein, by a first spray head 25, and preferably also a second spray head 26. The spray heads 25, 26, may be of conventional type, such as the commercially available "Water Pik" pulsating shower head (see U.S. Pat. No. 3,801,019), or minor modifications thereof. The spray heads 25, 26, that are used must be capable of setting up compression phases and interpulse decompression phases to the skin, which bounce off debris by a trampoline effect. Generally, the spray heads 25, 26, must be capable of delivering water jets at a pressure of about 70 psi at about 800 pulses per minute. A preferred range is 50 to 100 lbs./in$^2$ pressure, lower pressures being generally insufficient to set up the necessary compression/decompression cycle on the skin's surface, and higher pressures often being uncomfortable to the average person (although still effective). The pulsing rate preferably is between about 800 to 1200 pulses per minute, although somewhat lesser or greater pulsing rates may be employed in some situations as long as they are effective, at the pressure utilized, to set up the necessary compression/decompression cycle.

The first spray head 25 is mounted by a mounting means 27 in the chamber 12, and a second spray head 26 is mounted by a second mounting means 28 in the chamber 12 so that the jets of water from the heads 25, 26, intersect within the chamber 12 in the area at which the person utilizing the apparatus 10 has his/her hands placed (see FIG. 2 in particular). The hand openings 14, 14', and the spray head mounting means 27, 28, are positioned relative to each other in order to get the optimum cleansing action on the hands when placed within the chamber 12. The means 27, 28, may comprise metal collars, water repellant plastic glue, or any other suitable structure for holding the spray heads 25, 26, in positive position on the sphere 12.

The embodiment of the invention illustrated in the drawings provides the relative placement of the hand openings 14, 14', and the spray heads 25, 26, for effective hand cleaning, although variations from those positions may also achieve the desired results according to the invention. Preferably, the hand openings 14, 14', are horizontally spaced and substantially vertically coincident, being spaced along the circumference of the sphere 12 less than 180° apart, desirably less than about 90° apart—preferably 60° apart, although they may be provided with any spacing that facilitates ready placement of a person's hands within the sphere 12. The spray heads 25, 26, are preferably disposed in a common vertical plane, and mounted on the sphere 12 so that the jets emanating therefrom both have downward velocity components. The first spray head 25 most desirably is located between the hand openings 14, 14' (see FIG. 2 in particular) and is substantially in a common horizontal plane with the hand openings 14, 14' (slightly below the hand openings as illustrated in FIG. 1). Mounted in such a position, the first spray head 25 directs pulsating jets of water directly on both palms of the hands, and the hands are easily rotated to ensure that the pulsing jets impact directly on the bottoms of the hands. The second spray head 26 preferably is located about 90° along the circumference of the sphere from the first spray head 25, spacings of about 60° to about 135° apart being most effective. Located at the position illustrated in FIG. 1, the second spray head 26 directs pulsing jets of water directly on the top of the person's hands when placed in the chamber 12, and the person's hands may readily be rotated so that the jets impact directly on the backs of the hands.

Water under pressure may be delivered to the spray heads 25, 26, in any manner that achieves the desired end results. One specially suitable means 30 for supplying water under pressure to the spray heads 25, 26, comprises conduit means 31 for delivering water to the heads 25, 26, from a pressurized source of water 32 (a pump or conventional city water supply), with valve means 34 disposed in the conduit means 31 between the source 32 and the spray heads 25, 26. Foot operable control means 36, located beneath the chamber 12 in a position for ready actuation by the user of the apparatus 10, controls the operation of the valve means 34 to selectively supply, or interrupt the supply, of water from source 31 to spray heads 25, 26. The operation of the invention is not dependent upon water temperature, although obviously the water cannot be so hot that it irritates the skin of the user. Warm water preferably is supplied, and the valve means 34 may also provide mixing of water from conventional hot and cold water taps.

According to the method of the present invention, presurgical hand cleaning (or the like) is provided utilizing a chamber 12 with a pair of horizontally spaced hand openings 14, 14', therein, with a pair of pulsating water jet spray heads 25, 26, disposed in a common vertical plane and directed into the interior of the chamber 12 so that jets issuing therefrom have a downward velocity component and intersect at an angle of about 60° to about 135°, one of the spray heads 25 being located in substantially a common horizontal plane with the hand openings 14, 14', and between the hand openings, and a drain opening 16, leading to a sewer 20, being provided in the bottom of the chamber 12. The method comprises the steps of delivering pure water to the spray heads (as opposed to a recycled surgical soap solution of predetermined concentration, such as Betadine and pHisoHex solutions), issuing jets of pure water from the spray heads 25, 26, at about 50 to 100 psi at a pulsing rate of about 800 to 1200 pulses per minute while a person's hands are positioned within the chamber 12 (see FIG. 2) until the desired degree of cleanliness of the hands has been achieved (surgical cleanliness can be achieved); and withdrawing the water sprayed into the chamber 12 through the drain opening 16, and sewering it (at 20). This method eliminates the need for soap solution recirculating systems, yet achieves the desired degree of cleanliness.

While according to the present invention it is not necessary to utilize soap or a soap solution to achieve the desired degree of cleanliness, under some circumstances the individuals utilizing the apparatus 10 will feel the need to utilize some soap. To this end, a conventional surgical soap dispensing apparatus, shown schematically at 38 in the drawings, may be provided, for dispensing surgical soap onto the person's hands while positioned within the chamber 12. The dispensing means 38 preferably is provided in a top portion of the chamber 12, and is accessible by the person's hands when within the chamber 12. A supply of soap may be mounted directly on the globe 12, or the means 38 may be connected up to a remote supply of soap. Alternatively, the conduit 39 leading from valve 34 to conduit means 31 may have positioned therein a solid form 40 of sterilizing composition, such as a solid form of surgical soap. As the water impacts the soap, a small amount is carried with the water to the spray heads 25, 26. The conduit 39 may be transparent, and the entire conduit 39 replaced when the solid 40 is used up, or provision may be made for gaining access to the conduit 39 for replacing the solid 40. As a further alternative, the user of the apparatus 10 may apply an antiseptic foam, or the like, to his/her hands before placing them into the chamber 12.

It will thus be seen that according to the present invention, a simple, versatile, widely applicable apparatus and method have been provided for facilitating the washing of a person's hands more rapidly and efficiently, with less irritation, than conventionally. While the invention has been herein shown and described in what is presently conceived to be the most practical and preferred embodiment thereof, it will be apparent to those of ordinary skill in the art that may modifications may be made thereof within the scope of the invention, which scope is to be accorded the broadest interpretation of the appended claims so as to encompass all equivalent structures and methods.

What is claimed is:

1. Apparatus for facilitating the washing of a person's hands, comprising
   a chamber;
   means defining a pair of horizontally spaced and substantially vertically coincident openings in said chamber for receiving a person's hands therein;
   a pair of pulsating liquid jet spray heads capable of delivering liquid at generally about 50 psi at a pulsing rate of generally about 800 pulses per minute;
   means for mounting said heads in said chamber so that said heads direct jets of liquid therefrom into the volume defined by said chamber, and so that the jets of liquid therefrom intersect in the volume, and so that said heads are disposed in a common vertical plane between said chamber hand openings; and
   means defining a drain opening in a lower portion of said chamber.

2. Apparatus as recited in claim 1 further comprising means for dispensing soap into the chamber, said means provided in a top portion of said chamber.

3. Apparatus as recited in claim 1 further comprising conduit means for delivering water to said spray heads, and valve means operatively associated with said conduit means for selectively blocking or allowing passage of water to said spray heads from a source of pressurized water, and foot operable control means located beneath said chamber for controlling operation of said valve means.

4. Apparatus as recited in claim 1 further comprising means for supplying water under pressure to said spray heads, and foot operable control means located beneath said chamber for controlling operation of said water supplying means.

5. Apparatus as recited in claim 1 wherein said means for mounting said spray heads further comprise means for mounting said spray heads so that the jets issuing therefrom make an angle of about 60° to about 135° with respect to each other.

6. Apparatus as recited in claims 1 or 5 wherein said means for mounting said spray heads further comprise means for mounting said spray heads so that the jets issuing therefrom have a downward velocity component.

7. Apparatus as recited in claims 1 or 5 wherein said chamber is generally spherical, and wherein said means for mounting said spray heads further comprise means for mounting one of said spray heads so that it is in a common horizontal plane with said hand openings, and between said openings, and so that the other of said spray heads is above said hand openings; and wherein said means defining said hand openings further comprises means for defining said hand openings so that they are less than 180° apart around the circumference of said spherical chamber, and above a horizontal plane bisecting said spherical chamber.

8. Apparatus for facilitating the washing of a person's hands comprising
   a transparent, rigid, hollow sphere defining a chamber;
   means defining a drain opening in the bottom of said sphere, with a drainpipe leading downwardly from said sphere;
   support means substantially concentric with said drainpipe for supporting said sphere at a vertically raised position from a horizontal surface;
   means defining a pair of openings spaced horizontally along said sphere, in said sphere, for receiving a person's hands therein, the openings being less than about 90° apart;
   a first pulsating water jet spray head capable of delivering water at generally about 50 psi, at a pulsing rate of generally about 800 pulses per minute;
   means for mounting said first spray head so that it is substantially in a common horizontal plane with said hand openings, disposed between said hand openings;
   means for supplying water under pressure to said spray head; and
   foot-operable control means located beneath said sphere, adjacent the horizontal surface supporting said sphere, for controlling operation of said water supplying means.

9. Apparatus as recited in claim 8 further comprising a second pulsating spray head capable of delivering water at generally about 50 psi at a pulsing rate of generally about 800 pulses per minute; means for mounting said second pulsating spray head on said sphere in a common vertical plane with said first pulsating spray head so that it directs a jet of water into said chamber with a downward velocity component and so that it is disposed about 60° to about 135° around the circumference of said sphere from said first pulsating spray head.

10. A method of hand cleansing utilizing a chamber with a pair of horizontally spaced hand openings therein, with a pair of pulsating water jet spray heads disposed in a common vertical plane and directed into the interior of the chamber so that jets issuing therefrom have a downward velocity component and intersect at an angle of about 60° to about 135°, one of the spray heads being located in substantially a common horizontal plane with the hand openings and between the hand openings, and a drain opening being provided in the bottom of the chamber, said method comprising the steps of:
   delivering pure water to the spray heads,
   issuing jets of pure water from the spray heads at about 50 to 100 psi at a pulsing rate of about 800–1200 pulses per minute while a person's hands are positioned within the chamber, until the desired degree of cleanliness of the hands has been achieved, and
   withdrawing the water sprayed into the chamber through the drain opening, and sewering it.

11. A method as recited in claim 10 comprising the further step of dispensing surgical soap onto a person's hands while positioned within the chamber.

12. A method as recited in claim 10 comprising the further step of applying an antiseptic foam to the person's hands outside the chamber prior to the placement of the person's hands into the chamber.

13. A method as recited in claim 10 wherein the steps are practiced until surgical cleanliness is achieved.

* * * * *